US008827939B2

(12) United States Patent
Slatten

(10) Patent No.: US 8,827,939 B2
(45) Date of Patent: Sep. 9, 2014

(54) INFANT HEADWEAR FOR TREATING AN INFANT'S PERSISTENTLY MAINTAINED HEAD POSITION, SEEN IN CONDITIONS SUCH AS PLAGIOCEPHALY (BABY FLAT HEAD) AND TORTICOLLIS (WRY NECK)

(76) Inventor: Jeff Brian Slatten, Delta (CA)

( * ) Notice: Subject to any disclaimer, the term of this patent is extended or adjusted under 35 U.S.C. 154(b) by 293 days.

(21) Appl. No.: 12/659,986

(22) Filed: Mar. 26, 2010

(65) Prior Publication Data

US 2010/0252054 A1    Oct. 7, 2010

(51) Int. Cl.
*A61F 5/00*    (2006.01)
(52) U.S. Cl.
USPC ............................................ 602/17; 128/858
(58) Field of Classification Search
USPC ........... 602/17, 18; 128/857–858; 2/410, 411, 2/414, 418, 419, 421
See application file for complete search history.

(56) References Cited

U.S. PATENT DOCUMENTS

| | | | | |
|---|---|---|---|---|
| 6,238,413 | B1 * | 5/2001 | Wexler | 606/204.15 |
| 6,381,760 | B1 * | 5/2002 | Lampe et al. | 2/425 |
| 7,566,313 | B1 * | 7/2009 | Argenta | 602/17 |

* cited by examiner

*Primary Examiner* — Michael A. Brown

(57) ABSTRACT

An article of headwear to treat an infant's persistently maintained head position with respect to rotation about the cranial-caudal (head to toe) axis, seen in conditions such as plagiocephaly (baby flat head) and torticollis (wry neck). The headwear both permits and encourages an infant with a preferred head position to volitionally turn his or her head in several positions thereby promoting head and neck rotation and development of a naturally shaped cranium, thus treating or preventing torticollis and plagiocephaly respectfully. The infant headwear generally includes a head receiving member and positioning guide member. The head receiving member is placed on the infant's head and allows strategic placement of the positioning guide member. The positioning guide member increases the ability of the infant with a flat region to turn his or her head by re-establishing a round contour, and selectively increases cutaneous pressure in order to balance the variables influencing the infant's preferred head position.

13 Claims, 4 Drawing Sheets

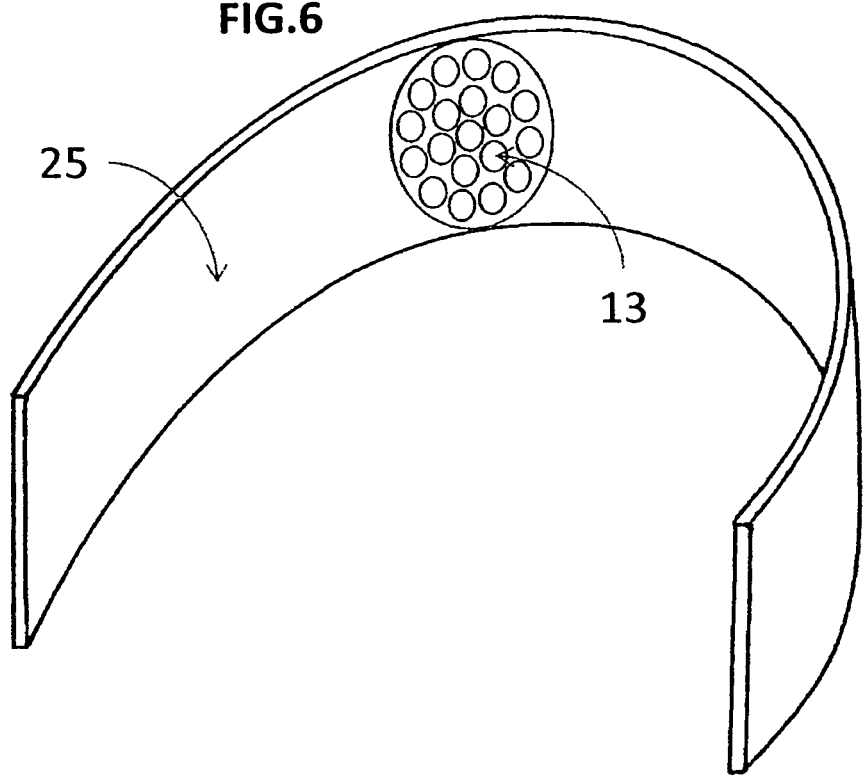

INFANT HEADWEAR FOR TREATING AN INFANT'S PERSISTENTLY MAINTAINED HEAD POSITION, SEEN IN CONDITIONS SUCH AS PLAGIOCEPHALY (BABY FLAT HEAD) AND TORTICOLLIS (WRY NECK)

FIELD OF THE INVENTION

This application relates to articles of infant headwear to treat an infant's persistently maintained head position with respect to rotation about the infant's cranial-caudal (head to toe) axis, seen in conditions such as plagiocephaly and torticollis.

BACKGROUND OF THE INVENTION

Two common disorders, torticollis and positional plagiocephaly, involve an infant persistently maintaining a particular head position with respect to rotation about the infant's cranial-caudal axis. Both conditions therefore cause a particular region of the infant's head to be persistently in contact with the lying or reclining surface; this region of the head is hereby defined as the habitual contact region. Constant pressure on a habitual contact region due to the pull of gravity may lead to irregular bone development.

Torticollis refers to a condition involving imbalanced neck musculature whereby an infant is predisposed to have their head turned to one specific side as a result of tighter musculature on one side of the neck with respect to the opposite side. Positional plagiocephaly is a condition where the bones of the infant's cranium grow abnormally due to prolonged pressure on a habitual contact region, causing a flat spot to develop at that region. A flat spot often occurs at a posterior-lateral aspect of the head or the posterior-central aspect of the head.

Because torticollis predisposes the head to be turned in one direction, creating a habitual contact region, it can lead to posterior-lateral positional plagiocephaly. Likewise, a flat region present on a posterior-lateral aspect of the infant's head creates a stable base for the infant's head and consequently promotes greater periods of unilateral head and neck rotation. A sequelae of prolonged periods of unilateral neck rotation is imbalanced neck musculature; thus plagiocephaly may lead to torticollis or reinforce a pre-existing torticollis. Because of the close association between the two conditions they often coexist.

Positional plagiocephaly and torticollis can range from very mild to very severe; more severe or prolonged conditions may lead to structural abnormalities in the cervical spine as the spine does not develop throughout a normal range of motion. As well, if the conditions are not treated, craniofacial dysplasia including facial deformities, ear discrepancies and temporomandibular joint problems may develop. Structural abnormalities may lead to functional deficits and or cosmetic concerns. Plagiocephaly is more likely to develop in the first few month of life as the cranium is generally more pliable at this time. This is especially the case if a flat region was present at birth, as an infant's head tends to settle on the flat region; subsequently, more time is spent with pressure on the flat region. This may be considered a self-perpetuating plagiocephaly.

There are several variables that affect an infant's preference to have their head turned toward the left or right: individual factors such as muscle tone, head shape, tissue length, and cutaneous sensitivity; and external factors such as the sleeping surface, visually interesting objects or people, and sounds, especially a parent's voice. If the fine balance is shifted in either direction the infant will tend to favor having his or her head turned toward that particular side. Conversely, the infant may develop a preference to maintain the head in a straight forward position. In this position the habitual contact region is at the posterior-central aspect of the infant's head. This often leads to a flat region over the posterior-central aspect of the infant's head.

Sudden Infant Death Syndrome and the American Academy of Pediatrics:

Rates of positional plagiocephaly have increased over the last decade after the American Academy of Pediatrics (AAP) made the recommendation to place infants in a supine position (on their backs) to sleep in order to reduce incidences of Sudden Infant Death Syndrome (SIDS). The present invention addresses the latest AAP recommendations concerning SIDS and positional plagiocephaly. These recommendations are discussed in more detail below.

Infants should continue to be placed to sleep in a supine position. This recommendation has been very successful in decreasing incidences of SIDS and is now considered the standard of care. However, infants sleeping supine has subsequently lead to increased incidences of positional plagiocephaly.

Infants should no longer be placed in a side lying position as they tend to roll into a more dangerous prone (on the belly) position.

Objects such as pillows, stuffed animals, and quilts should not be placed in the crib. Wedges and infant positioners should not be used. Sleeping clothing should be considered as an alternative to placing quilts in the crib but infants should be lightly dressed to prevent overheating.

To prevent positional plagiocephaly an infant's head position should be periodically adjusted. Infants should also not be left in reclined positions for prolonged periods of time such as in car seats or strollers as pressure on the back of the head in a reclined position can also contribute to positional plagiocephaly.

There is no evidence to suggest that infants should be repositioned if they are able to comfortably change their own position. It should be appreciated that any method that restricts an infant from rolling to a prone position may also restrict the infant from comfortably re-establishing a safer supine position.

Commercial devices designed to reduce the risk of SIDS should be avoided as none have been sufficiently tested to prove efficacy or safety.

Infants who are accustomed to sleeping on their backs are up to 18 times more likely to die from SIDS when inadvertently placed prone to sleep. This most often occurs under the care of an alternate caregiver. Therefore, it is recommended that infants always be placed to sleep supine, unless otherwise instructed by a medical doctor.

Sensory Integration:

Sensory integration was defined by Jean Ayres (2005) as "the organization of sensations for use." Infants use sensory information gained through their senses to make sense of their world and to determine how they are interacting with it. Sensory information is gathered through the five common senses: vision, hearing, olfaction, taste, and touch; and through an internal sensory system that detects the pull of gravity, body position and movement. An infant processes all the information received by his or her senses, typically unconsciously; analyses and organizes the information; then makes an appropriate response, such as moving a limb or turning his or her head.

Infant Growth and Development:

Infants learn by exploring their body, their environment and the interactions between their body and the environment.

If an infant can only interact with a limited part of their body and environment it may adversely affect learning, cognition, balance, and motor development. Similar adverse affects have occurred as a result of prolonged movement restriction, such as in cases of child neglect.

Jean Piaget (1896-1980), the pioneer of child cognitive development, described four stages of development cognitive development. Infants are at the primary, sensorimotor stage. In this first stage infants must experience and learn about the world through their senses and through movement. An infant's notion of causality emerges gradually by learning that they can have an effect on the world around them. An infant's ability to make adjustments to his or her own surroundings is critical to proper development and also provides them with a sense of being able to influence their environment. Unfortunately, several therapeutic devices in the past have required the parent, guardian, or healthcare provider to impose their own will on the child, to restrict their movement and to restrict their interactions with the environment.

The supine position has been implicated as the cause of increased incidences of positional plagiocephaly; however, it should be made clear that many infants sleep supine and still develop naturally shaped heads. Infants who freely move their heads while in supine position tend to develop naturally shaped craniums. It is a constant pressure to one region of the infant's skull, the habitual contact region, as a result of a maintained head position, that leads to positional plagiocephaly.

DESCRIPTION OF PRIOR ART

As previously noted, positional plagiocephaly often results secondary to parents judiciously following recommendations to prevent SIDS. However, paradoxically, previous art designed to prevent or correct positional plagiocephaly tends to increase the risk of SIDS and directly contravenes the latest AAP recommendations.

Previous art is not adequate as it tends to involve use of structures placed in the crib with the infant which can lead to suffocation, and often ineffective as mobile infants tend to move away from the devices; tends to prevent the infant from rolling back to a supine position, therefore maintaining the infant in a dangerous position; tends to compensate for neck rotation by simply imposing a counter rotated body position; does not address the primary problem of a maintained neck position, thus cannot prevent consequent neck problems nor encourage the infant to explore both sides of its body and environment; tends to be restricted to crib use and is not readily transferable to other environments such as a car seat or stroller; tends to be bulky, unsightly, and costly.

Previous art pertaining to positional plagiocephaly has thus far been focused on the following four methods: (1) apparatus that forces an infant to maintain a side lying position so that pressure is redistributed; (2) apparatus that the infant lies on or in configured to redistribute forces and restrict an infant in a supine position; (3) rigid devices placed on an infant's head to mold the bone into a predetermined shape; and (4) devices placed on an infant's head to disperse forces and restrict the infant's mobility. Examples of previous art in these categories are discussed in more detail below.

1) Apparatus that Forces an Infant to Maintain a Side Lying Position

Please visit U.S. Pat. Nos. 5,216,772, 5,272,780, 5,310, 245, and 5,341,531. Essentially these devices consist of two body pillows intended to keep infant on their sides. These devices are dangerous as items in the crib have been determined by the AAP to be a risk factor for Sudden Infant Death Syndrome. The AAP states clearly that all pillows, toys, and the like should not be placed in a crib with an infant. Any device that restricts an infant's movement also restricts re-establishment of a safe position and prevents head and neck rotation required for proper development of the cervical spine, muscles, and associated structures; it also prevents the infant from exploring and learning about its body and environment.

2) Apparatus that the Infant Lies on or in Configured to Redistribute Forces and Restrict an Infant in a Supine Position.

Please see U.S. Pat. Nos. 6,052,849, 6,321,403, 6,536,058 and application Ser. No. 11/684,604. These devices are purported to function by maintaining the infant in a supine position while dispersing forces to different regions of the head. Similar to the group 1 methods, these devices involve placement of the device in the crib with the infant which has been determined to be a hazard. As well, they are configured to restrict an infant's mobility. Importantly, the foregoing devices fail to address neck rotation.

One example of prior art maintains the infant's body in a supine position while maintaining the infant's head turned counter to the infant's preferred position and so, unlike others, does consider infant neck rotation. Please see U.S. Pat. No. 6,473,923. This infant positioner has a mat with two body pillows to force the infant to maintain a supine position and a wedge shaped head positioner such that the infant's head is forced to rotate toward the opposite side. This device is unsafe, however, as it involves placing a device with pillows in the crib, restricts the infants body movement and requires using a forceful method to maintain the infant's head in the counter position.

3) Rigid Devices Placed on an Infant's Head to Mold the Bone into a Predetermined Shape:

Please refer to U.S. Pat. No. 5,094,229 for a representative example. Cranial remodeling orthoses are often utilized when all other options have failed. The orthoses have proven to be effective but have several disadvantages. They are bulky, obtrusive, rigid, uncomfortable, and need to be worn for 23 hours a day. Fitting the orthosis is often very distressing to the infant. The orthosis typically cost thousands of dollars which, as considered a cosmetic device, are often not covered by health insurance. In addition, they must be utilized at an older age to ensure the infant's neck musculature can support the device; however, by this time, preventable deformation has already occurred. Moreover, skin breakdown and infection may occur as a result of the extended periods of use that are necessary for the devices to be effective.

4) Devices Placed on an Infant's Head to Disperse Forces and Restrict the Infant's Mobility Please see U.S. Pat. No. 6,592,536. Unlike other cranial remodeling orthoses, this helmet comprises a large protrusion far outside the contour of the infants head such that it "forces the infant to turn his head away" from the preferred position. The infant is a passive bystander, not an active participant, and will thus not learn to turn his or her head. Importantly, the large protrusion may prevent the infant from returning to a supine position if he or she has rolled to a dangerous prone position. Moreover, in all likelihood, the interaction of the large protrusion with the lying surface, combined with the infant's mobility, would tend to cause the device to be pulled off of the infant's head. The patent appears to address this concern by stating that the device is preferably secured to the infant's head using a chin strap; however, it must be noted that a chin strap is a risk factor for strangulation.

Please see U.S. Pat. No. 7,430,765. This previous art is in the form of a flexible hat that contains a protruding support cushion which surrounds a pressure relief region. Much like the U.S. Pat. No. 6,592,536 above, the infant is a passive bystander, the device is configured in such a way as to restrict movement, the large protrusion may prevent the infant from re-establishing a safe position, and the large protrusion will likely cause the device to be forced off of the infant's head.

USPTO Patent Application 20080184489 appears to be essentially the same as the above U.S. Pat. No. 7,430,765.

All of the previous art described above has been determined to be unsafe and assumes that the infant is just a passive object to be manipulated. There is a need for a simple, safe and inexpensive device that meets the recommendations of the AAP with respect to SIDS; allows for unrestricted and volitional head and neck movement; allows for self-regulated stretching of neck muscles to prevent injury; gives the infant a sense of control over their body and environment; can be utilized in the first few months while the infant's head is most vulnerable to deformation; and can be easily transferred to many environments such as bed, stroller, or car seat. The following summary describes the present unique invention; it does not fit into any of the four categories listed above.

SUMMARY OF THE INVENTION

The present invention provides a unique method and device to treat persistently maintained head position with respect to rotation about the infant's cranial-caudal axis seen in conditions such as plagiocephaly and torticollis without using forceful methods. The present invention applies a completely novel way of approaching the problem. Unlike previous art, the present invention recognizes the ability of an infant to be an active participant in his or her own therapy. The method and device simply adjust key variables that influence an infant's preferred head position so that the infant chooses new head positions.

The present invention allows the infant to develop awareness of his or her effect on the world and learn about causality, allows unrestricted head movement for the most natural shaping of the infant's cranium, facilitates development of full range of motion at the neck, and permits greater exploration of the infant's own body and environment.

The present invention, unlike previous art, is functional, unrestrictive, safe, natural, and affordable, meets current American Academy of Pediatric recommendations regarding SIDS and positional plagiocephaly, is non-cumbersome, attractive, easily laundered, and simple and easy to use.

The invention provides an article of headwear configured to permit and encourage the infant to rotate his or her head away from the current preferred direction facilitating forces to be distributed evenly across the infant's skull thus promoting a naturally shaped head. The headwear generally comprises: (1) a soft, flexible head receiving member (HRM) in the form of a hat, cap, toque, beanie or the like, sized and shaped to accommodate the infant's head; and (2) a unique position guiding member (PGM).

The HRM may be configured from any fabric, net, mesh or the like, waterproof material, or any combination of these materials. As well, the HRM may be constructed with one or more layers, or combination thereof.

The PGM is generally configured to have an outermost contour and an innermost contour. The outermost contour is configured to approximate the natural convex contour of the infant's head, hereby defined as the extrapolated contour. The PGM may project slightly away from the extrapolated contour in order to reduce the tendency for the infant's head to be maintained on a flat area.

Unlike previous art, the present invention is not configured to project substantially away from the infant's head such that it prevents rotation of an infant's neck. Thus, unlike previous art, the present invention is not intended to absolutely prevent an infant from assuming his or her preferred position or to force an infant to maintain a different set position. Rather, it is intended to adjust key variables while permitting an infant to voluntarily turn his or her head, in order that he or she will rest, and learn to rest, his or her head in a variety of position. Most importantly, unlike previous art, the device does not impede an infant from re-establishing a supine position if they have rolled to a more dangerous prone position.

The innermost contour of the PGM is configured to approximate the actual contour of the infant's head at the habitual contact region. For example, an infant who has developed a flat area requires a PGM that manifests a relatively flat innermost contour, whereas an infant with torticollis, who may have not yet developed positional plagiocephaly, requires a PGM that manifests a concave innermost contour. The thickness at the center of the PGM in these examples will thus be thicker or thinner respectively.

For infants with positional plagiocephaly the PGM is disposed over the flat area at the back of the infant's head and thus temporarily restores the natural contour of the cranium to prevent the head from getting stuck on the flat area. As much more strength and energy are required for an infant to turn his or her head off of a flat area, temporarily restoring roundness to the head increases the ease at which an infant can roll his or her head, hereby defined as rollability.

The innermost contour of the PGM is configured to adjust the amount of cutaneous pressure and relative comfort the infant experiences. Generally, this is accomplished by configuring the innermost contour of the PGM with a plurality of projections. Decreasing the surface area increases focal pressure at the projections; zero pressure is experienced at interstitial areas. Depending on the magnitude of an infant's preferred head position the innermost contour may have any number of said projections or lack thereof. Thus the PGM has at least two possible roles. First, it permits the infant to turn his or her head off of the flat area by increasing its rollability and, second, it encourages the infant to rest his or her head on different regions of the skull.

The edge formed at the intersection of the innermost contour and the outermost contour is hereby defined as the perimeter of the positioning guide member. The perimeter may exhibit a variety of shapes including but not limited to circular, oval, elliptical, and polygonal, or any combination thereof.

The PGM may comprise a variety of materials including but not limited to silicone, natural and synthetic rubber, plastic, any natural or synthetic fibers or materials, or any combination thereof. The PGM may be constructed from a separate piece of material or several pieces. For non limiting examples: one PGM embodiment is molded as one piece of silicone; another PGM may comprise a plurality of separate members; another PGM is comprised with a core material and a peripherally located material. The PGM may be formed by molding, pressing, by the removal of material, shaping of natural of synthetic fibers, or any other practical method.

The PGM may be located between layers of the HRM, or located within a pocket attached to a layer of the HRM. Further, the PGM may be directly attached to the outer surface, the inner surface, embedded in, surrounded by, or integral to the HRM. In one embodiment the PGM may exist independently of a HRM such that it may be attached to any HRM in any manner known in the art such as but not limited to Velcro®. Another embodiment is used to test an infant's response to the external stimulus of the PGM and to fit an appropriate PGM; it generally comprises a wide plastic band integral to a PGM or affixed to a PGM so that the embodiment may be readily sanitized. Bands with incremental variations of the PGM are configured to secure temporarily and comfortably to an infant's head in order to allow healthcare providers or caregivers to determine the suitability, appropriate size, hardness, and number of projections of a particular PGM.

The PGM is aligned over the habitual contact region simply by rotating the HRM around the cranial-caudal axis of the infant's head. The PGM can be aligned along the cranial-caudal axis by adjusting the distance between the PGM and the top of the HRM. In one embodiment this is accomplished by altering the position in which a knot at the top of the hat member is tied, either higher or lower, such that the positioning guide member is disposed directly over the habitual contact region and turning up or down the turned up portion of the HRM accordingly. Another embodiment adjusts the distance between the PGM and the top of the HRM by closing snaps, Velcro®, or other appropriate fastening devices located in gradations near the top of the HRM.

Infants, like adults, position themselves according to the most comfortable position, and infants, like adults, acquire preferred positions as a result of individual and external factors. Lying directly on the PGM is not painful to the infant; it merely offers a less comfortable position for the infant than the other positions at the infant's disposal. Unlike previous art, an objective is to facilitate learning such that the infant places his or her head in multiple positions rather than stifling the infant's preference using forceful methods. As infants are able to learn very quickly, the present invention, unlike previous art, does not require an extended period of use. For any infant, the use of the present invention should be discontinued if, after an appropriate period of time, it has not demonstrated to at least reduce the amount of time an infant remains in the original preferred position. The present invention may not be suitable for an infant unable to demonstrate sufficient volitional head and neck rotation to external stimuli; at this stage the infant may benefit from manual therapy, surgical intervention and or a cranial remodeling orthosis mentioned above.

The protected method associated with the present invention involves providing detailed instruction regarding sizing, precautions, limitations, adjustments, schedule of use, and providing the headwear.

BRIEF DESCRIPTION OF THE DRAWING

FIG. 6 illustrates an alternative embodiment of the invention for testing an infant's response to the external stimulus of a positioning guide member and to determine the positioning guide member's appropriate size, hardness, and number of projections.

DETAILED DESCRIPTION OF THE INVENTION

Figure 1:
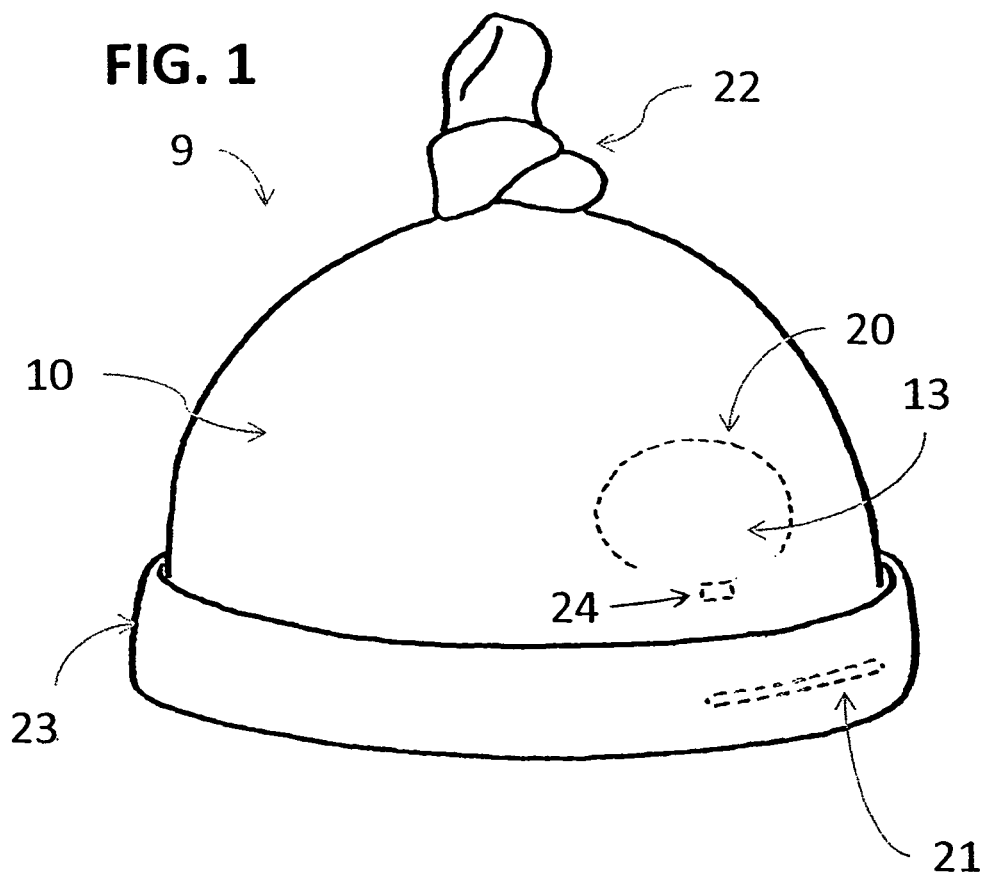
FIG. 1 illustrates a posterior perspective of an exemplary embodiment of the invention.

FIG. 1 illustrates an exemplary embodiment of an infant headwear 9 for the prevention or treatment of positional plagiocephaly and or torticollis. The headwear 9 comprises a soft, flexible Head Receiving Member (HRM) 10 in the form of but not limited to a hat, toque, beanie, or cap, sized and shaped to accommodate an infant's head 8. The HRM 10 may comprise any number of suitable materials, such as but not limited to: natural and synthetic fabric, which may or may not exhibit one or more apertures; woven, net, mesh materials or the like; waterproof materials; or any combination of said materials. The HRM 10 may be constructed with one or more layers of the said materials or combination thereof. For ease of explanation, and in no way limiting, the HRM 10 illustrated in FIG. 1 comprises an outer layer 11 and an inner layer 12 as viewed in the double layered embodiment of FIG. 2. As a non-limiting example, one embodiment comprises a solid fabric outer layer 11 with a soft, breathable inner layer 12. Further, the outer layer may or may not comprise one or more ventilation openings with or without a suitable closure system in the form of a zipper, snaps, or the like to permit temperature regulation. Alternatively, the ventilation opening may be sufficiently large such that a substantial amount of the top region of the HRM 10 comprises a single breathable layer.

Figure 3A:
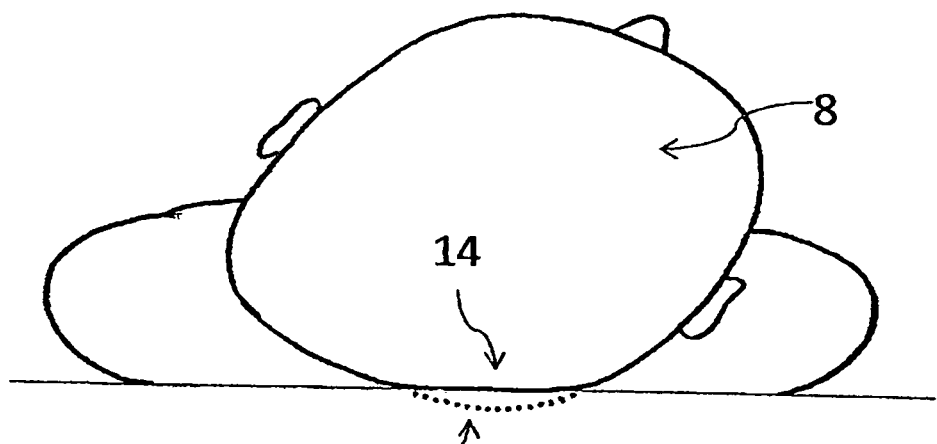
FIG. 3a illustrates a superior perspective of an infant lying supine, relative to the infant's anatomical position, exhibiting a persistently maintained head position and positional plagiocephaly.
Figure 3B:
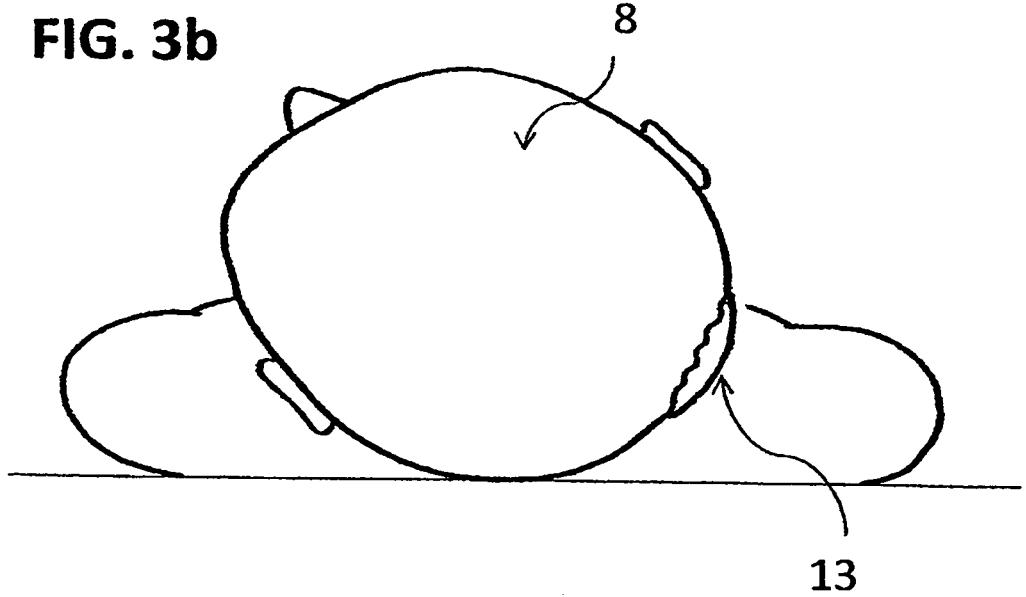
FIG. 3b illustrates a superior perspective of an infant lying supine, relative to the infant's anatomical position, demonstrating the position of the positioning guide member (without the head receiving member for the purpose of clarity), and exhibiting a new head position.

FIG. 3a and FIG. 3b illustrate the implementation of the Positioning Guide Member (PGM) 13 (for the purpose of clarity the HRM 10 is not displayed). FIG. 3a illustrates the infant's head in a persistently maintained position, resting on the flattened habitual contact region 14 without a PGM 13 and dashed lines indicate the extrapolated contour 15 of the infant's head. FIG. 3b demonstrates the PGM 13 disposed over the flattened habitual contact region 14 and the re-establishment of a natural convex shape with consequently increased rollability. The resulting head position illustrated in FIG. 3b is merely one of the many different positions the infant may decide to rest his or her head on after integration of all relevant sensory information.

Figure 2:
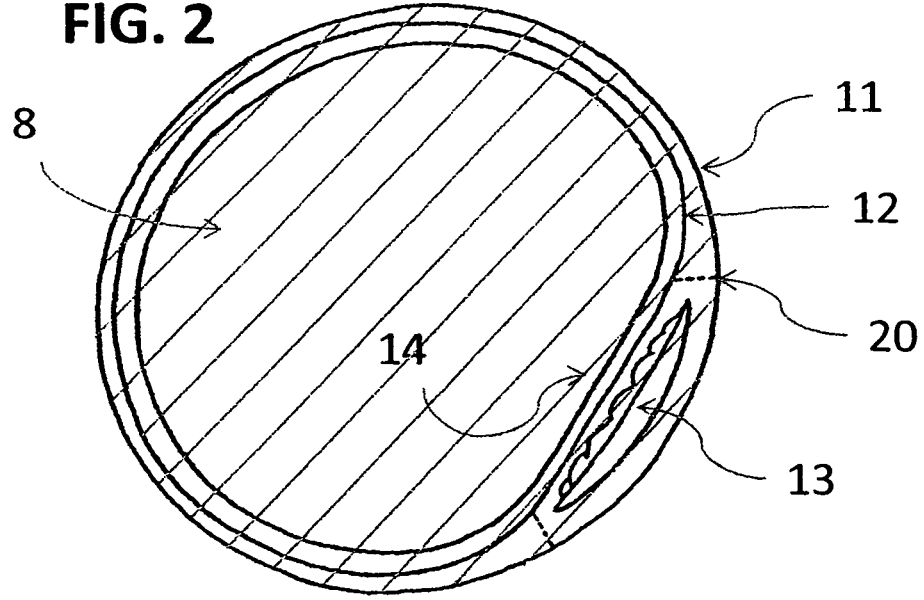
FIG. 2 illustrates a superior cross-sectional perspective, relative to the infant's anatomical position, of an exemplary embodiment of the invention in use.
Figure 4A:
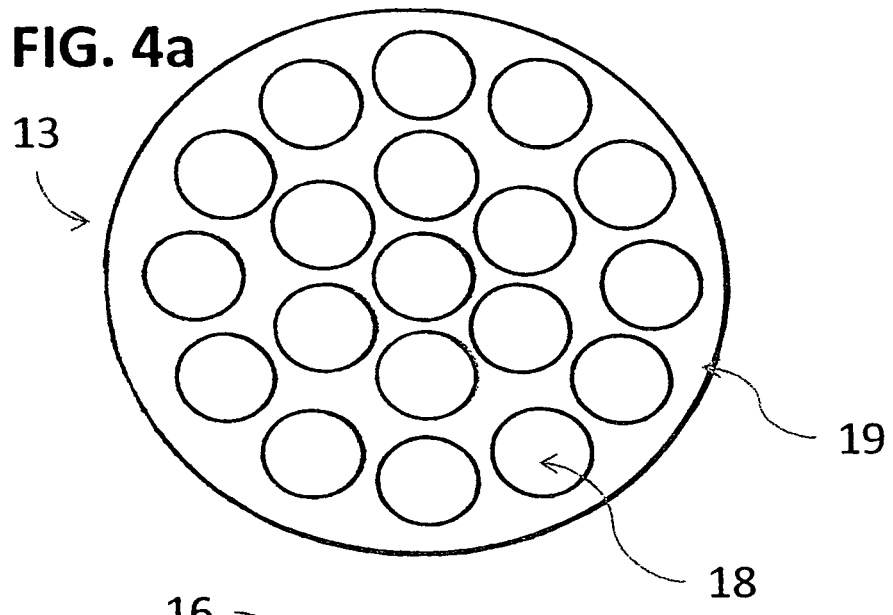
FIG. 4a illustrates an enlarged innermost perspective of the preferred positioning guide member.
Figure 4B:
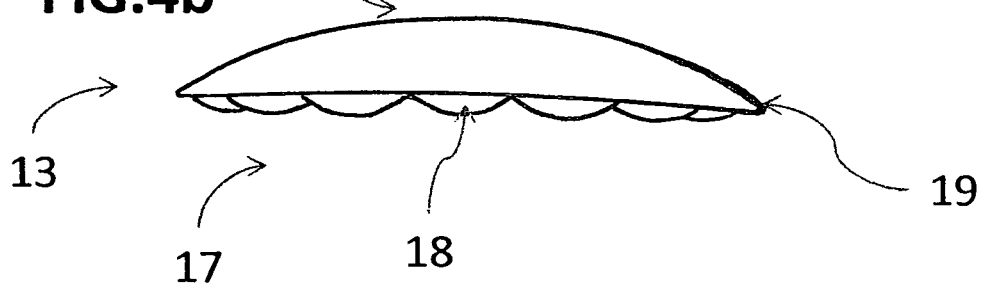
FIG. 4b illustrates an enlarged lateral perspective of the preferred positioning guide member.

FIG. 4a illustrates an enlarged innermost view of the preferred PGM 13 and FIG. 4b illustrates an enlarged lateral view of the preferred PGM 13. The PGM 13 may comprise any, or combination of any, suitable material including but not limited to silicone, natural or synthetic rubbers, natural or synthetic fibers, and plastics. The size of the PGM 13 is determined by the circumference of the infant's head and extent of flattening. As illustrated in FIG. 2 & FIG. 3b the PGM 13 occupies the space between the actual contour of the habitual contact region 14 and the extrapolated contour 15. The PGM is generally configured to have an outermost contour 16 and an innermost contour 17.

The PGM's outermost contour 16 is configured to approximate the extrapolated contour 15 of the infant's head 8 or project slightly away from the extrapolated contour 15 in order to reduce the tendency for the infant's head to be maintained on the flattened habitual contact region 14. Unlike previous art the headwear 9 is not configured to have any part project substantially away from the infant's head such that it prevents the rotation of an infant's neck. Thus, unlike previous art, the present invention is not configured to prevent an infant from assuming his or her preferred position nor is it configured to force an infant to maintain a different position. Rather, the headwear 9 is configured to modify key variables, rollability and comfort, while permitting an infant to voluntarily turn his or her head, in order that he or she learn to rest his or her head in a variety of positions. Critically, unlike previous art, the headwear 9 is configured such that it will not impede an infant from re-establishing a supine position if they manage to roll to a more dangerous prone position.

The innermost contour 17 of the PGM 13 is configured to adjust the amount of pressure (and thus comfort) experienced by the habitual contact region 14 of the infant's head 8 by altering the exposed surface area that the habitual contact region 14 is subjected to. Generally, this is accomplished by configuring the innermost contour 17 of the PGM 13 with a plurality of projections 18. The projections 18 may be configured by molding, pressing, removal of material, or other practical method. Depending on the magnitude of the infant's preferred head position, the innermost contour 17 may have any number of projections 18 or lack thereof.

The perimeter 19 of the PGM 13 may be configured in a variety of shapes including but not limited to circular, oval, elliptical, polygonal, spiral, or combination thereof.

Figure 5:
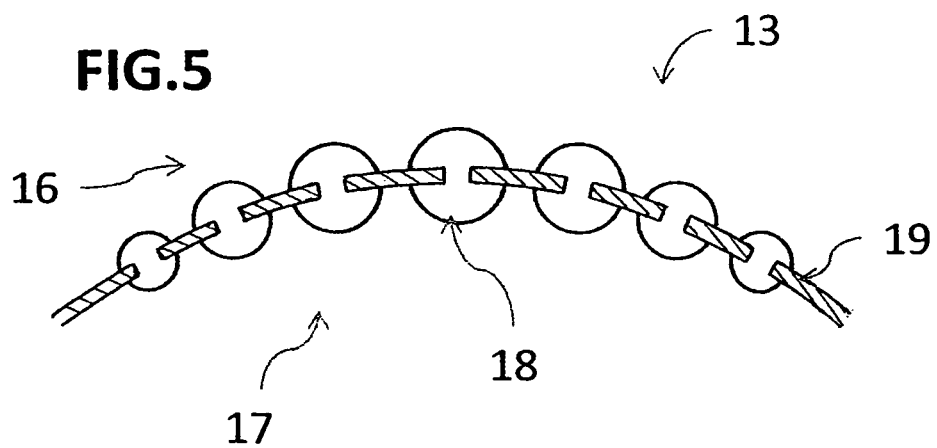
FIG. 5 illustrates a lateral perspective of an alternative positioning guide member, comprising a plurality of separate members.

The PGM 13 may comprise one or more individual members. For non limiting examples, one PGM 13 comprises a core material and a peripherally located material (the core material consisting of a softer material or gel); another PGM 13 as seen in FIG. 5 comprises a plurality of projections 18 associated with an assemblage of individual members. As illustrated in FIG. 1 & FIG. 2 the PGM 13 of the exemplary embodiment is located between layers of the HRM 10, joined together with peripherally located pocket stitching 20. In the exemplary embodiment, the PGM 13 may be inserted or removed via an access aperture 21 concealed behind the turned up portion 23 of the HRM 10, the PGM is retained with a closure 24 comprising at least one snap, Velcro®, or other suitable method. In a different embodiment the PGM 13 is located within a pocket attached to the inner or outer surface of one layer of the HRM 10. In other embodiments the PGM 13 is attached directly to the outer or inner surface of one HRM 10 layer. Alternatively, the PGM 13 may be embedded in, surrounded by, or integral to the HRM 10. In one embodiment the PGM 13 exists independently of a HRM 10 and is attached to an appropriate HRM 10 in any manner known in the art, such as but not limited to a clip or Velcro®. FIG. 6 illustrates a PGM 13 integral to or affixed to a wide band 25, preferably comprising sanitizable plastic, for the purposes of testing an infant's response to external stimulus and to determine the positioning guide member's 13 appropriate size, firmness, and number of projections 18.

The PGM 13 of the exemplary embodiment is aligned over the habitual contact region 14 by rotating the headwear 9 around the infant's cranial-caudal axis. The PGM 13 is aligned along the cranial-caudal axis by adjusting the distance between the PGM 13 and the top of the HRM 10. In the exemplary embodiment illustrated in FIG. 1 this is accomplished by adjusting the position of the knot 22 tied at the most distal aspect of the HRM 10 and by turning up or down the turned up portion 23 of the PGM 13 accordingly, such that the PGM 13 is disposed directly over the habitual contact region 14. Another embodiment adjusts the distance between the PGM 13 and the top of the HRM 10 utilizing snaps, Velcro®, or other appropriate fasteners located in gradations near the most distal aspect of the HRM 10.

What is claimed is:

1. An article of flexible headwear for treating an infant's persistently maintained head position with respect to rotation about the cranial-caudal axis comprising:
   a head receiving member, sized and shaped to approximate the size and shape of the infant's head; and
   a positioning guide member, to be disposed over the habitual contact region;
   wherein the positioning guide member comprises an outermost contour and an innermost contour such that the outermost points of the positioning guide member approximate the extrapolated contour of the infant's head and the innermost points of the positioning guide member approximate the actual contour of the infant's head at the habitual contact region.

2. The article of flexible headwear of claim 1, wherein the head receiving member is configured as a hat, cap, toque, skull-cap, or beanie.

3. The article of flexible headwear of claim 1, wherein the head receiving member comprises at least one layer of material selected from a group consisting of fabrics, net, mesh, woven material, waterproof material, and combinations thereof.

4. The article of flexible headwear of claim 1, wherein the positioning guide member comprises a material selected from the group consisting of plastic, natural rubber, synthetic rubber, and combinations thereof.

5. The article of flexible headwear of claim 1, wherein the innermost contour of the positioning guide member comprises a plurality of balls configured to determine the amount of cutaneous pressure the infant experiences.

6. The article of flexible headwear of claim 1, wherein the perimeter of the positioning guide member has a shape that is selected from a group consisting of circular, oval, elliptical, polygonal and a combination thereof.

7. The article of flexible headwear of claim 1, wherein the positioning guide member is positioned in said pocket formed by stitching together adjacent layers of the head receiving member.

8. The article of flexible headwear of claim 1, wherein the positioning guide member is positioned in said pocket formed by stitching a separate pocket panel to a layer of the head receiving member.

9. The article of flexible headwear of claim 1, wherein the positioning guide member is affixed directly to a layer of the head receiving member.

10. An article of flexible headwear for treating an infant's persistently maintained head position with respect to rotation about the cranial-caudal axis comprising:
    a head receiving member, sized and shaped to approximate the size and shape of the infant's head; and
    a positioning guide member to be disposed over the habitual contact region;
    the positioning guide comprises a single body having outer most contour and an inner most contour having a plurality of projections located therein to apply pressure to the infant's head, said single body is located within a pocket, attached to the head receiving member.

11. The article of flexible headwear of claim 10, wherein the outermost contour comprises a convex shape from the group consisting of a hemispherical geometry and an inverted cup-shaped geometry, the cross-section of which reveals a parabola.

12. The article of flexible headwear of claim 10, wherein the said plurality of projections reduce the tendency for the infant to rest his or her head on the habitual contact region, permits voluntary rotation of the neck, and does not impede re-establishment of a supine position.

13. A method of treating an infant's persistently maintained head position with respect to rotation about the cranial-caudal axis comprising the steps of:
- disposing an article of flexible headwear on an infant's head comprising a head receiving member, sized and shaped to approximate the size and shape of the infant's head, and a positioning guide member that comprises and outermost contour and innermost contour such that the outermost points of the positioning guide member approximates or protrudes from the extrapolated contour of the infant's head, and the innermost points of the positioning guide member approximate the actual contour of the infant's head at the habitual contact region;
- adjusting the headwear in order to dispose the positioning guide member over the habitual contact region;
- placing the infant wearing the flexible headwear in a supine position on a lying or reclining surface.

\* \* \* \* \*